United States Patent
De La Poterie et al.

(12) 
(10) Patent No.: US 6,254,877 B1
(45) Date of Patent: *Jul. 3, 2001

(54) TRANSFER-FREE COSMETIC COMPOSITION COMPRISING A DISPERSION OF NON-FILM-FORMING POLYMER PARTICLES IN A PARTIALLY NONVOLATILE LIQUID FATTY PHASE

(75) Inventors: Valérie De La Poterie, Le Chatelet en Brie; Nathalie Mougin, Paris, both of (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/218,073

(22) Filed: Dec. 22, 1998

(30) Foreign Application Priority Data

Dec. 22, 1997 (FR) .................................. 97 16252

(51) Int. Cl.$^7$ ....................................... A61K 7/48
(52) U.S. Cl. ...................... 424/401; 424/64; 424/70.7; 424/78.02
(58) Field of Search ........................... 424/401, 64, 70.7, 424/78.02

(56) References Cited

U.S. PATENT DOCUMENTS

| | | | |
|---|---|---|---|
| 5,505,937 | * | 4/1996 | Castrogiovanni et al. . |
| 5,945,095 | * | 8/1999 | MOugin et . |

FOREIGN PATENT DOCUMENTS

| | | |
|---|---|---|
| 0 195 575 A1 | 9/1986 | (EP) . |
| 0 497 144 A1 | 8/1992 | (EP) . |
| 0 602 905 A2 | 6/1994 | (EP) . |
| 709083 * | 5/1996 | (EP) . |
| 2123290 * | 2/1984 | (GB) . |
| WO 97/01321 | 1/1997 | (WO) . |

* cited by examiner

*Primary Examiner*—Raj Bawa
(74) *Attorney, Agent, or Firm*—Oblon, Spivak, McClelland, Maier & Neustadt, P.C.

(57) ABSTRACT

The present invention relates to a care and/or make-up anhydrous composition, in particular a cosmetic, dermatological, hygienic or pharmaceutical composition, for the skin, which may be provided in the form of a cast product or a gel comprising at least one, in particular pulverulent, coloring matter and a dispersion of non-film-forming polymer particles which are surface-stabilized in a partially nonvolatile liquid fatty phase. Depending on the quantity of polymer and of nonvolatile oil, it is possible to obtain, on the lips or the skin, a nonfatty soft film having remarkable transfer-free properties, while imparting a very high degree of comfort. The invention also relates to the use of this dispersion in such a composition.

73 Claims, No Drawings

TRANSFER-FREE COSMETIC COMPOSITION COMPRISING A DISPERSION OF NON-FILM-FORMING POLYMER PARTICLES IN A PARTIALLY NONVOLATILE LIQUID FATTY PHASE

BACKGROUND OF THE INVENTION

1. Field of the Invention

The present invention relates to a composition containing a non-film-forming polymer dispersible in a fatty phase, intended, in particular, for use in the cosmetic, dermatological, pharmaceutical and hygienic fields. More particularly, the invention relates to a transfer-free care and/or make-up composition for the skin of both the face and the human body, for the mucous membranes such as the lips and the inside of the lower eyelids, or alternatively for the superficial body growths such as the eyelashes, the eyebrows, the nails and the hair.

This composition may be provided in particular in the form of a product cast as a stick or in a dish such as lipsticks or lip balms, cast foundations, concealers, eyeshadows or blushers, in the form of a paste or a cream which is fluid to a greater or lesser degree such as fluid foundations or lipsticks, eyeliners, compositions for protecting against sunlight or for coloring the skin.

2. Description of the Background

The make-up or care products for the skin or the lips of human beings such as foundations or lipsticks generally contain fatty phases such as waxes and oils, pigments and/or fillers and, optionally, additives such as cosmetic or dermatological active agents. They may also contain so-called "pasty" products, of soft consistency, which make it possible to obtain pastes, colored or otherwise, to be applied with a brush.

These compositions, when they are applied to the skin or the lips, have the disadvantage of transferring, that is to say of becoming deposited at least in part, leaving marks, onto certain supports with which they may be brought into contact, and in particular a glass, a cup, a cigarette, clothing or the skin. This results in poor persistence of the applied film, requiring regular renewed application of the foundation or lipstick composition. Moreover, the appearance of these unacceptable marks especially on blouse collars can prevent some women from using this type of make-up.

For several years, cosmeticians have been interested in lipstick compositions and, more recently, in foundation compositions which are "transfer-free". Thus, Shiseido describes in JP-A-61-65809 "transfer-free" lipstick compositions containing a siloxy silicate resin (with a three-dimensional network), a volatile silicone oil with a cyclic silicone chain and pulverulent fillers. Likewise, Noevier has described in JP-A-62-61911 "transfer-free" lipstick, eyeliner and foundation compositions containing one or more volatile silicones combined with one or more hydrocarbon waxes.

Although exhibiting enhanced "transfer-free" properties, these compositions have the disadvantage of leaving on the lips, after evaporation of the silicone oils, a film which becomes uncomfortable over time (feeling of dryness and tightness), turning a number of women away from using this type of lipstick. To enhance the comfort of this type of composition, nonvolatile silicone or nonsilicone oils may be added to them, but in this particular case, there will be a reduction in "transfer-free" efficiency.

More recently, Procter & Gamble described, in WO-A-96/36323, water-in-oil emulsion-type mascara compositions which exhibit long retention, resistance to water and which do not leave marks. These compositions contain, inter alia, a water-insoluble polymer generally called a latex, combined with a surfactant of the alkyl or alkoxy dimethicone copolyol type, hydrocarbon oils, pigments and fillers as well as waxes.

The compositions based on silicone oils and silicone resins as well as those based on latex provide matt colored films. However, women are nowadays looking for glossy products especially for coloring the lips. Furthermore, the transfer-free properties of the films deposited are not perfect. In particular, substantial pressure or rubbing leads to a decrease in the color of the deposit and to redeposition on the support brought into contact with these films.

In addition, EP-A-497144 and FR-A-2,357,244 describe so-called "transfer-free" compositions containing a styrene-ethylene-propylene block polymer combined with waxes, light or volatile oils and pigments. These compositions have the disadvantage of not being comfortable to any great extent, of having poor cosmetic properties, and of being difficult to formulate. Moreover, the "transfer-free" properties of these compositions are only average.

The need, therefore, still exists for a composition that does not exhibit the above disadvantages, and having in particular complete "transfer-free" properties even during substantial or intensive pressure or rubbing, an appearance which is glossy to a greater or lesser degree, in line with the wishes of the consumer, which does not cause the skin or the lips to which it is applied to dry out over time.

SUMMARY OF THE INVENTION

The inventor has observed, quite surprisingly, that the use of a non-film-forming polymer dispersible in a partially nonvolatile liquid fatty phase, in a cosmetic, dermatological, pharmaceutical or hygienic composition, provides a glossy cohesive deposit with a very good retention, which does not transfer at all, which is resistant to water, while being very pleasant to apply and to wear throughout the day. The deposit is in particular neither fatty nor dry, is flexible and nonsticky.

An object of the present invention is therefore to provide a composition for topical application, comprising a liquid fatty phase and at least one coloring agent, characterized in that it also comprises at least 2% by weight, relative to the total weight of the composition, of non-film-forming polymer dispersible in the liquid fatty phase, where the fatty phase contains, based on the total weight of the composition, at most 40% of nonvolatile liquid fatty components.

This composition is in particular a cosmetic, dermatological, hygienic or pharmaceutical composition. This composition therefore contains ingredients compatible with the skin, the mucous membranes and the keratinous fibres or superficial body growths.

The present invention also provides a composition provided in the form of a cast product and comprising at least one cosmetic, dermatological, hygienic or pharmaceutical liquid fatty phase and at least one wax which is solid at room temperature, which also comprises at least 2% by weight, relative to the total weight of the composition, of non-film-forming polymer dispersible in the liquid fatty phase, where the fatty phase contains, based on the total weight of the composition, at most 40% of nonvolatile liquid fatty components.

The polymer used in the present invention may be of any type. It is thus possible to use a free-radical polymer, a polycondensate, or even a polymer of natural origin and mixtures thereof. The polymer may be chosen by persons skilled in the art according to its properties and according to the desired subsequent application of the composition.

The subject of the invention is also a composition comprising a cosmetic, dermatological, hygienic or pharmaceutical liquid fatty phase, at least 2% by weight, relative to the total weight of the composition, of non-film-forming polymer dispersible in the fatty phase, and at least one active agent chosen from cosmetic, dermatological, hygienic or pharmaceutical active agents, where the liquid fatty phase contains at most 40% by weight of nonvolatile liquid fatty components.

Another subject of the invention is the use, in or for the manufacture of a composition in the form of a cast product and comprising at least one cosmetic, dermatological, hygienic or pharmaceutical liquid fatty phase, of which at most 40% by weight, relative to the total weight of the composition, is nonvolatile, and at least one wax which is in particular solid at room temperature, of at least 2% by weight, relative to the total weight of the composition, of non-film-forming polymer dispersible in the said liquid fatty phase, for reducing, or even suppressing, the transfer of the composition film deposited on the mucous membranes such as the lips and/or on the skin.

Another subject of the invention is the use, in or for the manufacture of a cosmetic, dermatological, pharmaceutical or hygienic composition, of at least 2% by weight, relative to the total weight of the composition, of non-film-forming polymer dispersible in a liquid fatty phase, the latter containing at most 40% of the total weight of the composition of non-volatile liquid fatty phase, relative to the total weight of the composition, for reducing, or even suppressing, the transfer of the composition film deposited on the mucous membranes and/or the skin of human beings onto a support brought into contact with the film.

Another subject of the invention is the use, in or for the manufacture of a composition for topical application, comprising a liquid fatty phase of which at most 40% by weight, relative to the total weight of the composition, is nonvolatile, and at least one ingredient chosen from cosmetic, dermatological, hygienic and pharmaceutical active agents, coloring agents and mixtures thereof, of at least 2% by weight, relative to the total weight of the composition, of non-film-forming polymer dispersible in the liquid fatty phase, for reducing, or even suppressing, the transfer of the composition film deposited on the skin and/or the mucous membranes such as the lips.

The subject of the invention is also a method for the cosmetic care of or the application of make-up to the lips or the skin, consisting in applying respectively to the lips or the skin a cosmetic composition as defined above.

The subject of the invention is also a cosmetic method for limiting, or even suppressing, the transfer of a make-up or care composition for the skin or the lips onto a support different from the said skin and the said lips, containing a liquid fatty phase and at least one ingredient chosen from coloring matter, cosmetic, dermatological, hygienic and pharmaceutical active agents and mixtures thereof, consisting in introducing into the liquid fatty phase at least 2% by weight, relative to the total weight of the composition, of non-film-forming polymer dispersible in the said liquid fatty phase, the latter containing at most 40% by weight, relative to the total weight of the composition, of nonvolatile fatty phase.

A more complete appreciation of the invention and many of the attendant advantages thereof will be readily obtained as the same becomes better understood by reference to the following detailed description.

DETAILED DESCRIPTION OF THE INVENTION

A term "non-film-forming polymer" refers to a polymer not capable of forming, alone, an isolatable film. This polymer makes it possible, in combination with an oil-type nonvolatile compound, to form a continuous and homogeneous deposit on the skin and the mucous membranes.

Preferably the polymer is provided in the form of dispersed particles which are surface-stabilized by at least one stabilizer. One advantage of using a dispersion of particles in a composition of the invention is that the particles remain in the form of elemental particles, without forming agglomerates, in the fatty phase, which would not be the case with inorganic particles of nanometric size. Another advantage of the polymer dispersion is the possibility of obtaining very fluid compositions (of the order of 130 centipoises), even in the presence of a high level of polymer.

Yet another advantage of such a dispersion is that it is possible to calibrate, as required, the size of the polymer particles, and to modulate their size "polydispersity" during synthesis. It is thus possible to obtain particles of very small size, which are invisible to the naked eye when they are in the composition and when they are applied to the skin or the lips. This would not be possible with pigments in particulate form, their constitution not making it possible to modulate the mean size of the particles.

It has, furthermore, been observed that the compositions according to the invention exhibit particularly advantageous qualities of spreadability and adhesiveness on the skin, the semi-mucous membranes or the mucous membranes, as well as a smooth and pleasant feel. These compositions have, in addition, the advantage of being easily removed especially with a conventional make-up-removing milk. This is quite remarkable since previously known compositions with high "transfer-free" properties are very difficult to remove. In general, they are sold with a specific make-up-removing product, which introduces an additional constraint for the user.

The compositions according to the invention therefore advantageously comprise a stable dispersion of generally spherical particles of at least one non-film-forming polymer, in a physiologically acceptable liquid fatty phase. These dispersions may in particular be provided in the form of nanoparticles of polymers in a stable dispersion in the said fatty phase. The nanoparticles are preferably of between 5 and 600 nm in size, given that above about 600 nm the dispersions of particles become much less stable. This size range includes all specific values and subranges therebetween, including 10, 25, 50, 100, 200, 300, 400 and 500 nm.

Yet another advantage of the dispersion of polymer of the composition of the invention is the possibility of varying the glass transition temperature (Tg) of the polymer or of the polymeric system (polymer plus additive of the plasticizing type), and of thus passing from a soft polymer to a polymer which is hard to a greater or lesser degree, allowing the mechanical properties of the compositions to be adjusted depending on the application envisaged.

When the polymer has a glass transition temperature which is too high for the desired application, it may be combined with a plasticizer so as to lower this temperature of the mixture used. The plasticizer may be chosen from the plasticizers customarily used in the field of application and in particular from the compounds capable of being solvents for the polymer.

The polymers which can be used in the composition of the invention preferably have a molecular weight (weight-average) on the order of 2000 to 10,000,000 and a (Tg) of −100° C. to 300° C.

This molecular weight range includes all specific values and subranges therebetween, including 5,000, 10,000, 25,000, 50,000, 100,000, 250,000, 300,000, 500,000, 750,000 1,000,000, 2,000,000, 5,000,000 and 8,000,000. This Tg range includes all specific values and subranges therebetween, including −75, −50, −25, −10, −5, 0, 5, 10, 25, 50, 75, 100, 150, 200 and 250° C.

Among the non-film-forming polymers, there may be mentioned free-radical, vinyl or acrylic, optionally cross-linked homopolymers or copolymers preferably having a Tg greater than or equal to 40° C., such as polymethyl methacrylate, polystyrene or polytert-butylacrylate.

In a nonlimiting manner, the polymers of the invention may be chosen from the following polymers or copolymers: polyurethanes, acrylic polyurethanes, polyureas, polyurea-polyurethanes, polyester-polyurethanes, polyether-polyurethanes, polyesters, polyester amides, fatty chain polyesters, alkyds; acrylic and/or vinyl polymers or copolymers; acrylic-silicone copolymers; polyacrylamides; silicone polymers, fluorinated polymers and mixtures thereof.

The liquid fatty phase in which the polymer is dispersed may consist of any cosmetically or dermatologically acceptable, and more generally physiologically acceptable, oil chosen in particular from oils of inorganic, animal, plant or synthetic origin, carbonaceous oils, hydrocarbon oils, fluorinated oils and/or silicone oils, alone or in the form of a mixture insofar as they form a homogeneous and stable mixture and are compatible with the use envisaged.

"Liquid fatty phase" refers to any nonaqueous medium which is liquid at room temperature. "Volatile fatty phase" refers to any nonaqueous medium capable of evaporating from the skin or the lips, at room temperature, in less than one hour.

Nonvolatile liquid fatty phase which can be used in the invention, include hydrocarbon oils such as paraffin oil or liquid petroleum jelly, vison oil, turtle oil, soya bean oil, perhydrosqualene, sweet almond oil, calophyllum oil, palm oil, grapeseed oil, sesame oil, maize oil, parleam oil, arara oil, rapeseed oil, sunflower oil, cottonseed oil, apricot oil, castor oil, avocado oil, jojoba oil, olive oil or cereal germ oil; esters of lanolic acid, oleic acid, lauric acid or stearic acid; fatty esters, such as isopropyl myristate, isopropyl palnitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl or diglyceryl triisostearate; higher fatty acids such as myristic acid, palmitic acid, stearic acid, behenic acid, oleic acid, linoleic acid, linolenic acid or isostearic acid; higher fatty alcohols such as cetanol, stearyl alcohol or oleyl alcohol, linoleyl or linolenyl alcohol, isostearyl alcohol or octyl dodecanol; silicone oils such as polydimethylsiloxane (PDMS), which are optionally phenylated, such as phenyl trimethicones, or which are optionally substituted with optionally fluorinated aliphatic and/or aromatic groups, or with functional groups such as hydroxyl, thiol and/or amine groups; polysiloxanes modified with fatty acids, fatty alcohols or polyoxyalkylenes, fluorinated silicones and perfluorinated oils.

One or more oils which are volatile at room temperature and atmospheric pressure may optionally be used. These volatile oils have for example a steam pressure at ambient temperature and pressure of, preferably, from $10^{-3}$ to 300 mm Hg, provided that the boiling point is >30° C. These volatile oils facilitate in particular the application of the composition to the skin, the mucous membranes and the superficial body growths. These oils may be hydrocarbon oils, silicone oils optionally comprising alkyl or alkoxy groups at the end of the silicone or pendant chain.

As volatile silicone oil which can be used in the invention, there may be mentioned linear or cyclic silicones having from 2 to 7 silicon atoms, these silicones optionally containing alkyl or alkoxy groups having from 1 to 10 carbon atoms such as $C_8$–$C_{16}$ isoparaffins and in particular isododecane. These volatile oils represent preferably from 0 to 97.5% of the total weight of the composition, and more preferably from 5 to 85%. These ranges include all specific values and subranges therebetween, including 0.5, 1, 2, 8, 10, 15, 25, 30, 50, 60, 70, 80, 90 and 95% by weight.

In a specific embodiment of the invention, the liquid fatty phase is chosen from the group comprising:

the nonaqueous liquid compounds having an overall solubility parameter according to the HANSEN solubility space of less than 17 $(MPa)^{1/2}$, or the monoalcohols having an overall solubility parameter according to the HANSEN solubility space of less than or equal to 20 $(MPa)^{1/2}$, or mixtures thereof.

The overall solubility parameter, overall δ, according to the HANSEN solubility space is defined in the article "Solubility parameter values" by Eric A. Grulke from "Polymer Handbook" 3rd edition, Chapter VII, pages 519–559, incorporated herein by reference, by the equation:

$$\delta=(d_D^2+d_P^2+d_H^2)^{1/2}$$

in which characterizes the LONDON dispersive forces resulting from the formation of dipoles induced during molecular shocks, $d_P$ characterizes the DEBYE interactive forces between permanent dipoles, $d_H$ characterizes the specific interactive forces (hydrogen, acid/base, donor/acceptor type bonds, and the like). The definition of the solvents in the three-dimensional solubility space according to HANSEN is described in the article by C. M. HANSEN: "The three-dimensional solubility parameters" J. Paint Technol. 39, 105 (1967), incorporated herein by reference.

Among the liquid fatty phases having an overall solubility parameter according to the HANSEN solubility space of less than or equal to 17 $(MPa)^{1/4}$, there may be mentioned vegetable oils formed by esters of fatty acids and polyols, in particular triglycerides, such as sunflower, sesame or rapeseed oil, or the esters derived from long-chain acids or alcohols (that is to say having from 6 to 20 carbon atoms), in particular the esters of formula RCOOR' in which R represents the residue of a higher fatty acid containing from 7 to 19 carbon atoms and R' represents a hydrocarbon chain containing from 3 to 20 carbon atoms, such as palmitates, adipates and benzoates, in particular diisopropyl adipate. There may also be mentioned the hydrocarbons and in particular paraffin oils, liquid petroleum jelly, or hydrogenated polyisobutylene, isododecane, or alternatively the "ISOPARs", volatile isoparaffins. There may also be mentioned the silicone oils such as polydimethylsiloxanes and polymethylphenylsiloxanes, optionally substituted with optionally fluorinated aliphatic and/or aromatic groups, or with functional groups such as hydroxyl, thiol and/or amine groups, and the volatile, in particular cyclic, silicone oils. There may also be mentioned the solvents, alone or in the form of a mixture, chosen from (i) linear, branched or cyclic esters having more than 6 carbon atoms, (ii) ethers having more than 6 carbon atoms, (iii) ketones having more than 6 carbon atoms. Monoalcohols having an overall solubility parameter according to the HANSEN solubility space of less than or equal to 20 $(MPa)^{1/2}$ are understood to mean the aliphatic fatty alcohols having at least 6 carbon atoms, the hydrocarbon chain containing no substitution group. As monoalcohols according to the invention, there may be mentioned oleyl alcohol, decanol, dodecanol, octadecanol and linoleyl alcohol.

The choice of the nonaqueous medium is made by persons skilled in the art as a function of the nature of the monomers constituting the polymer and/or of the nature of the stabilizer, as indicated below. In particular, it is possible to use apolar or weakly polar oils such as vegetable oils of the long carbon chain-containing triglyceride type (apricot oil, jojoba oil) or the long carbon chain-containing esters such as octyldodecyl neopentanoate, the alkanes such as parleam oil, and the silicone oils. It is also possible to use the nonaqueous media described in FR-A-2,710,646, incorporated herein by reference.

Furthermore, the total liquid fatty phase in which the polymer is dispersed may represent from 30% to 98% of the total weight of the composition and preferably from 30 to 75%. These ranges for the total liquid fatty phase include all specific values and subranges therebetween, including 35, 40, 45, 50, 60, 70, 80, 85, 90 and 95% of the total weight of the composition. The nonvolatile part represents at least 0.5% and in practice from 1 to 30% of the total weight of the composition. These ranges for the nonvolatile part include all specific values and subranges therebetween, including 2, 3, 5, 10, 15, 20 and 25% of the total weight of the composition.

The polymer dispersion may be manufactured as described in EP-A-749747, incorporated herein by reference. The polymerization may be carried out in dispersion, that is to say by precipitation of the polymer being formed, with protection of the particles formed with a stabilizer.

A mixture is therefore prepared comprising the initial monomers as well as a free-radical initiator. This mixture is dissolved in a solvent called, in the remainder of the present description, "synthesis solvent". While the fatty phase is a nonvolatile oil, the polymerization may be carried out in an apolar organic solvent (synthesis solvent) and then the nonvolatile oil added (which should be miscible with the synthesis solvent) and the synthesis solvent selectively distilled.

A synthesis solvent is therefore chosen such that the initial monomers, and the free-radical initiator, are soluble therein, and the particles of polymer obtained are insoluble therein so that they precipitate therein during their formation. In particular, the synthesis solvent may be chosen from the alkanes such as heptane, isododecane or cyclohexane.

When the chosen fatty phase contains a volatile oil, the polymerization may be directly carried out in the said oil which therefore also plays the role of synthesis solvent. The monomers should also be soluble therein, as well as the free-radical initiator, and the polymer obtained should be insoluble therein.

The monomers are preferably present in the synthesis solvent, before polymerization, in an amount of 5–20% by weight of the reaction mixture. The entire monomers may be present in the solvent before the beginning of the reaction, or a portion of the monomers may be added as the polymerization reaction progresses.

The free-radical initiator may be in particular azo-bis-isobutyronitrile or tert-butylperoxy-2-ethylhexanoate.

The polymer particles are surface-stabilized as the polymerization progresses by means of a stabilizer which may be a block polymer, a graft polymer and/or a random polymer, alone or in the form of a mixture. The stabilization may be carried out by any known means, and in particular by direct addition of the block polymer, graft polymer and/or random polymer, during the polymerization.

The stabilizer is preferably also present in the mixture before polymerization. However, it is also possible to add it continuously, in particular when the monomers are also added continuously. It is possible to use 2–30% by weight of stabilizer relative to the initial mixture of monomers, and preferably 5–20% by weight.

When a graft and/or block polymer is used as stabilizer, the synthesis solvent is chosen such that at least a portion of the graft or block units of the polymer-stabilizer is soluble in the solvent, the other portion of the graft or block units not being soluble therein. The polymer-stabilizer used during the polymerization should be soluble or dispersible in the synthesis solvent. Furthermore, a stabilizer is preferably chosen whose insoluble block or graft units exhibit some affinity for the polymer formed during the polymerization.

Among the graft polymers, there may be mentioned the silicone polymers grafted with a hydrocarbon chain; the hydrocarbon polymers grafted with a silicone chain.

Also suitable are the graft copolymers having, for example, an insoluble backbone of the polyacrylic type with soluble grafts of the polyhydroxy stearic acid type, copolymers based on acrylates or methacrylates of $C_1$–$C_4$ alcohols, and acrylates or methacrylates of $C_8$–$C_{30}$ alcohols.

As block or graft block copolymers comprising at least one polyorganosiloxane type block and at least one block of a free-radical polymer, there may be mentioned the acrylic/silicone type graft copolymers which may be used in particular when the nonaqueous medium contains silicone.

As block or graft block copolymers comprising at least one polyorganosiloxane type block and at least one polyether, there may be used the dimethicone copolyols such as those sold under the name "DOW CORNING 3225C" by DOW CORNING, the lauryl methicones such as those sold under the name "DOW CORNING Q2-5200" by DOW CORNING.

As block or graft block copolymers comprising at least one block resulting from the polymerization of diene, hydrogenated or nonhydrogenated, and at least one block of a vinyl polymer, there may be mentioned the block copolymers, in particular of the "diblock" or "triblock" type, of the polystyrene/polyisoprene, polystyrene/polybutadiene type such as those sold under the name "LUVITOL HSB" by BASF, of the polystyrene/copoly(ethylene-propylene) type such as those sold under the name "KRATON" by Shell Chemical Co. or alternatively of the polystyrene/copoly (ethylene-butylene) type.

As block or graft block copolymers comprising at least one block resulting from the polymerization of diene, hydrogenated or nonhydrogenated, and at least one block of an acrylic polymer, there may be mentioned poly(methyl methacrylate)/polyisobutylene bi- or triblock copolymers or graft copolymers with a poly(methyl methylacrylate) backbone and with polyisobutylene graft units.

As block or graft block copolymers comprising at least one block resulting from the polymerization of diene, hydrogenated or nonhydrogenated, and at least one block of a polyether, there may be mentioned the polyoxyethylene/polybutadiene or polyoxyethylene/polyisobutylene bi- or triblock copolymers.

When a random polymer is used as stabilizer, it is chosen so that it has a sufficient quantity of groups making it soluble in the synthesis solvent envisaged.

It is thus possible to use copolymers of acrylates or of methacrylates of $C_1$–$C_4$ alcohols, and of acrylates or of methacrylates of $C_8$–$C_{30}$ alcohols. There may be mentioned in particular the stearyl methacrylate/methyl methacrylate copolymer.

When the synthesis solvent is apolar, it is preferable to choose, as stabilizer, a polymer providing the most complete covering of the particles possible, several chains of polymers-stabilizers then becoming adsorbed on a particle of polymer obtained by polymerization.

In this case, it is then preferable to use as stabilizer either a graft polymer or a block polymer, so as to have a better interfacial activity. Indeed, the block or graft units insoluble in the synthesis solvent provide a more voluminous covering at the surface of the particles.

Moreover, when the liquid fatty phase comprises at least one silicone oil, the stabilizing agent is preferably chosen from the group consisting of the block or graft block copolymers comprising at least one polyorganosiloxane type block and at least one block of a free-radical polymer or of a polyether or of a polyester.

When the liquid fatty phase does not comprise a silicone oil, the stabilizing agent is preferably chosen from the group consisting of:

(a) the block or graft block copolymers comprising at least one polyorganosiloxane type block and at least one block of a free-radical polymer or of a polyether or of a polyester, (b) the copolymers of $C_1$–$C_4$ alcohol acrylates or methacrylates, and of $C_8$–$C_{30}$ alcohol acrylates or methacrylates, (c) the block or graft block copolymers comprising at least one block resulting from the polymerization of diene, hydrogenated or nonhydrogenated, and at least one block of a vinyl or acrylic polymer or of a polyether or of a polyester, or mixtures thereof.

The dispersions obtained according to the invention may then be used in a composition, in particular a cosmetic, dermatological, pharmaceutical and/or hygienic composition, such as a care or make-up composition for the skin or the lips, or alternatively a hair composition or an antisun or skin coloring composition.

Surprisingly, the composition according to the invention contains a nonvolatile liquid fatty phase providing comfort upon application and throughout the day, while exhibiting complete transfer-free properties. Indeed, it is known to persons skilled in the art that the presence of nonvolatile oils is inconsistent with transfer-free properties. Thus, the inventor found that it was possible to introduce into a composition containing a non-film-forming polymer one or more nonvolatile oils, the quantity of nonvolatile oil(s) in the composition not exceeding 40% by weight, relative to the total weight of the composition, and preferably not exceeding 35% and more preferably not exceeding 30% by weight.

In other words, the transfer-free properties are advantageously obtained for a nonvolatile oil/non-film-forming polymer (as dry matter) weight ratio ranging from 0.30 to 0.60 and better still from 0.40 to 0.45. These ranges include all specific values and subranges therebetween, including 0.35, 0.50 and 0.55. Above a nonvolatile oil/polymer ratio of 0.60, a fatty and sticky film is obtained. In addition, the transfer-free properties may be comparable to known compositions.

Moreover, the transfer-free property increases with the quantity of polymer dispersible in the liquid fatty phase. In practice, the polymer may represent, as active material, up to 60% (as active material or as dry matter) of the total weight of the composition. This range for the amount of polymer includes all specific values and subranges therebetween, including 3, 5, 10, 15, 20, 25, 30, 35, 40, 45, 50 and 55% by weight. By using over 12% by weight, of polymer active material and of nonvolatile oil active material, in the composition, a complete transfer-free film is obtained. Between 2% and 12%, the transfer-free effect is notable without, however, being complete. It is therefore possible to adapt the transfer-free properties as desired, which was not possible with the transfer-free compositions of the prior art, without damaging the comfort quality of the film deposited.

The composition may advantageously comprise coloring matter which may comprise pulverulent compounds or fat-soluble colorants, for example in an amount of 0.01 to 70% of the total weight of the composition. The pulverulent compounds may be chosen from the pigments and/or the pearlescent agents and/or the fillers normally used in cosmetic or dermatological compositions. Advantageously, the pulverulent compounds represent from 0.1 to 40% of the total weight of the composition and better still from 1 to 30%. The lower the quantity of pulverulent compounds, the greater the transfer-free and comfort qualities. The fact that the transfer-free properties increase as the quantity of pulverulent compounds decreases is highly surprising. Indeed, up until now, the transfer-free properties of the prior art compositions increased with the quantity of pulverulent compounds. Conversely, their lack of comfort and their dryness on the skin or the mucous membranes increased.

Preferably, the pigment/polymer weight ratio is <1, preferably ±0.9 and more preferably ±0.5. These ranges for the pigment/polymer weight ratio include all specific values and subranges therebetween, such as 0.01, 0.02, 0.05, 0.1, 0.2, 0.3, 0.4, 0.6, and 0.8.

The composition of the invention may advantageously comprise at least 30% by weight, relative to the total weight of the composition, of total liquid fatty phase. Below 30%, a granular and pulverulent texture is obtained. This is not very desirable when it is sought to obtain a homogeneous, nongranular creamy, gel-like or stick-like appearance.

The pigments may be white or colored, inorganic and/or organic. There may be mentioned, among the inorganic pigments, titanium dioxide, optionally surface-treated, zirconium or cerium oxides, as well as iron or chromium oxides, manganese violet, ultramarine blue, chromium hydrate and ferric blue. Among the organic pigments, there may be mentioned carbon black, pigments of the D & C type, and lacquers based on carmine, barium, strontium, calcium or aluminium.

The pearlescent pigments may be chosen from the white pearlescent pigments such as mica coated with titanium or with bismuth oxychloride, the colored pearlescent pigments such as mica-titanium with iron oxides, mica-titanium with in particular ferric blue or chromium oxide, mica-titanium with an organic pigment of the abovementioned type as well as pearlescent pigments based on bismuth oxychloride.

The fillers may be inorganic or organic, lamellar or spherical. There may be mentioned talc, mica, silica, kaolin, nylon powders, poly-β-alanine and polyethylene, Teflon, lauroyl lysine, starch, boron nitride, tetrafluoroethylene polymer powders, hollow microspheres such as Expancel (Nobel Industrie), polytrap (Dow Corning) and microbeads of silicone resin (tospearls from Toshiba, for example), precipitated calcium carbonate, magnesium carbonate and hydrocarbonate, hydroxyapatite, hollow silica microspheres (SILICA BEADS from MAPRECOS), glass or ceramic microcapsules, metallic soaps derived from organic carboxylic acids having from 8 to 22 carbon atoms, preferably from 12 to 18 carbon atoms, for example zinc, magnesium or lithium stearate, zinc laurate, magnesium myristate.

The fat-soluble colorants are, for example, Soudan red, DC Red 17, DC Green 6, β-carotene, soybean oil, Soudan brown, DC Yellow 11, DC Violet 2, DC Orange 5, quinoline yellow. They may represent from 0.01 to 20% of the weight of the compositions, and better still from 0.1 to 6%. These ranges include all specific values and subranges therebetween, including 0.02, 0.05, 1, 2, 5, 10 and 15% by weight.

The polymer of the composition of the invention allows the formation of a film on the skin, the lips and/or the mucous membranes, forming a network, trapping the coloring matter (including the fillers) and/or the active agents. Depending on the relative quantity of coloring matter used relative to the quantity of stabilized polymer used, it is possible to obtain a film which is glossy to a greater or lesser degree and which is transfer-free to a greater or lesser degree. Unlike known compositions, the film obtained is not solely due to the entanglement of the polymeric chains, but rather to the trapping of the oil by the chains of the polymeric stabilizers.

As cosmetic, dermatological, hygienic or pharmaceutical active agents which can be used in the composition of the invention, there may be mentioned moisturizers, vitamins, essential fatty acids, sphingolipids and sunscreens. These active agents are used in the usual quantity for humans and in particular at concentrations of 0.001 to 20% of the total weight of the composition. This range includes all specific values and subranges therebetween, including 0.002, 0.005, 0.1, 0.2, 0.5, 1, 2, 5, 10 and 15% by weight.

The composition according to the invention may, furthermore, comprise, depending on the type of application envisaged, constituents conventionally used in the fields considered, which are present in a quantity appropriate for the desired galenic form.

In particular, it may comprise, in addition to the liquid fatty phase in which the polymer is stabilized, additional fatty phases which may be chosen from waxes, oils, gums and/or pasty fatty substances, of plant, animal, inorganic or synthetic origin, or even containing silicone, and mixtures thereof.

Among the solid waxes at room temperature which may be present in the composition according to the invention, there may be mentioned hydrocarbon waxes such as beeswax, 10 Carnauba wax, Candelilla wax, Ouricoury wax, Japan wax, sugar cane or cork fibre waxes, paraffin or lignite waxes, microcrystalline waxes, lanolin wax, Montan wax, ozokerites, polyethylene waxes, waxes obtained by Fischer-Tropsch synthesis, hydrogenated oils, fatty esters and glycerides which are concrete at 25° C. It is also possible to use silicone waxes, among which there may be mentioned alkyl, alkoxy and/or esters of polymethylsiloxane. The waxes may be provided in the form of stable dispersions of colloidal particles of wax as can be prepared according to known methods, such as those of "Microemulsions Theory and Practice", L. M. Prince Ed., Academic Press (1977), pages 21–32, incorporated herein by reference. As liquid wax at room temperature, jojoba oil may be used.

The waxes may be present in an amount of 0–50% by weight in the composition and preferably from 10 to 30%. These ranges include all specific values and subranges therebetween, such as 0.2, 0.5, 1, 2, 5, 15, 20, 25, 30, 40 and 45% by weight.

The composition may comprise, in addition, any additive customarily used in such compositions, such as thickeners, antioxidants, perfumes, preservatives, surfactants, fat-soluble polymers such as polyalkylenes, in particular polybutene, polyacrylates and silicon polymers compatible with the fatty phase as well as the polyvinylpyrrolidone derivatives. Of course those skilled in the art will be careful to choose such additional compounds, and/or their quantity, such that the advantageous properties of the composition according to the invention are not, or not substantially, adversely affected by the addition envisaged.

In a specific embodiment of the invention, the compositions according to the invention may be prepared in the customary manner by persons skilled in the art. They may be provided in the form of a cast product and, for example, in the form of a stick or rod, or in the form of a dish which can be used by direct contact or with a sponge. In particular, they find application as cast foundation, cast blusher or eyeshadow, lipstick, care base or balm for the lips, concealers. They may also be provided in the form of a soft paste, with a dynamic viscosity at 25° C. of the order of 1 to 40 Pa.s or alternatively of a gel, or a cream which is fluid to a greater or lesser degree. They may also consist of foundations or lipsticks, antisun or skin coloring products.

The compositions of the invention are advantageously anhydrous, and may contain, relative to the total weight of the composition, less than 5% of water. They may therefore be provided in particular in oily gel, oily liquid or oil, paste or stick form or alternatively in vesicular dispersion form containing ionic and/or nonionic lipids. These galenic forms are prepared according to the customary methods in the fields considered.

These compositions for topical application may constitute in particular a cosmetic, dermatological, hygienic or pharmaceutical composition for the protection, treatment or care of the face, the neck, the hands or the body (for example anhydrous care cream, antisun oil, body gel), a make-up composition (for example make-up gel) or an artificial tanning composition.

Having generally described this invention, a further understanding can be obtained by reference to certain specific examples which are provided herein for purposes of illustration only and are not intended to be limiting unless otherwise specified.

EXAMPLES

Example 1: Polymeric Dispersion

A dispersion of polymethyl methacrylate cross-linked with ethylene glycol dimethacrylate is prepared in isododecane according to the method of Example 2 of EP-A-749 746, incorporated herein by reference, replacing ISOPAR L with isododecane. A dispersion of polymethyl methacrylate particles which are surface-stabilized in isododecane with a polystyrene/copoly(ethylene-propylene) diblock block copolymer sold under the name KRATON G1701 (Shell), having a dry matter content of 19.7% by weight and a mean particle size of 135 nm (polydispersity: 0.05) and a Tg of 100° C., is thus obtained. This copolymer is non-film-forming at room temperature.

Example 2: Foundation

A foundation having the following composition is prepared in fluid form:

| | |
|---|---|
| dispersion according to Example 1 | 83.0 g |
| apricot oil | 7.0 g |
| pigments | 10.0 g |

The pigments contain a mixture of DC Red 27, DC Red 7, DC Red 36, black iron oxide and brown iron oxide.

The pigment/polymer ratio is 0.6.

The composition is prepared by simply mixing the various constituents at room temperature after grinding the pigments in the oils. A foundation is obtained which is easy to apply, and which allows the production of a comfortable, soft and nonsticky film. This film is, in addition, completely "transfer-free". It is perfectly resistant to water and can be removed with a conventional make-up-removing oil.

A sensory test was carried out with this foundation on several people in comparison with a known foundation (Colorstay from Revlon), containing volatile oils and a silicone resin with a three-dimensional network as described in EP-A-602 905. The transfer-free test was carried out under the following conditions: application of the foundation to the face and the neck using half the face and half the neck, drying in the open air for 10 minutes, fitting a collaret made of fabric around the neck for 30 minutes. The transfer-free properties are noted from 0 to 7; the higher the figure, the greater the transfer of the foundation.

The foundation of the present invention received the average mark of 3 against the average mark of 5 for the known foundation.

Furthermore, the people in the test judged the product of the invention to be easy to apply, very slippery, conferring a homogeneous and adherent make-up, having a very high covering power with a transparency effect. The pores are smooth and the complexion is uniform. The people in the test gave it the mark 5 (out of 7) in the make-up result. The texture of the product is judged to be fluid and pleasant upon application. The make-up removal is carried out with a conventional make-up remover (Bifacil from Chez Lancôme) without leaving marks.

Example 3: Foundation

The following composition is prepared:

| | |
|---|---|
| dispersion of Example 1) | 75.6 g |
| parleam oil | 6.4 g |
| nylon powder (filler) | 8.0 g |
| yellow iron oxide | 1.1 g |
| brown-yellow iron oxide | 0.6 g |
| black iron oxide | 0.3 g |
| titanium oxide | 8.0 g |

A foundation which may be applied to the body, especially the neck, and the face is obtained. The make-up is natural, matt, resistant to water and has very good transfer-free properties.

The pigment/polymer ratio is 0.67.

Obviously, numerous modifications and variations of the present invention are possible in light of the above teachings. It is therefore to be understood that within the scope of the appended claims, the invention may be practiced otherwise than as specifically described herein.

This application is based on French Patent application Ser. No. 97-16252, filed on Dec. 22, 1997, and incorporated herein by reference.

What is claimed is:

1. A composition suitable for topical application, comprising:
    a liquid fatty phase, containing, based on the total weight of the composition, at most 40% by weight of nonvolatile liquid fatty components;
    from 2 to 60% by weight, based on the total weight of the composition, of surface-stabilized non-film-forming polymer particles, which polymer particles are dispersed in said fatty phase and stabilized at their surface,
    wherein the polymer is selected from the group consisting of radical polymers. polycondensates and polymers of natural origin, and mixtures thereof; and
    at least one coloring agent.

2. A composition in the form of a cast product, comprising:
    at least one cosmetic, dermatological, hygienic or pharmaceutical liquid fatty phase, containing, based on the total weight of the composition, at most 40% by weight of nonvolatile liquid fatty components;
    at least one solid wax; and
    from 2 to 60% by weight, based on the total weight of the composition, of surface-stabilized non-film-forming polymer particles, which polymer particles are dispersed in said fatty phase and stabilized at their surface,
    wherein the polymer is selected from the group consisting of radical polymers. polycondensates and polymers of natural origin, and mixtures thereof.

3. A composition, comprising:
    a cosmetic, dermatological, hygienic or pharmaceutical liquid fatty phase containing, based on the total weight of the composition, at most 40% by weight of nonvolatile liquid fatty components;
    from 2 to 60% by weight, based on the total weight of the composition, of surface-stabilized non-film-forming polymer particles, which polymer particles are dispersed in said fatty phase and stabilized at their surface,
    wherein the polymer is selected from the group consisting of radical polymers, polycondensates and polymers of natural origin, and mixtures thereof; and
    at least one active agent selected from the group consisting of cosmetic, dermatological, hygienic and pharmaceutical active agents.

4. The composition of claim 2, further comprising at least one coloring agent.

5. The composition of claim 3, further comprising at least one coloring agent.

6. The composition of claim 1, wherein the polymer is selected from the group consisting of polyurethanes, acrylic polyurethanes, polyureas, polyurea-polyurethanes, polyester-polyurethanes, polyether-polyurethanes, polyesters, polyester amides, fatty chain polyesters, alkyds, acrylic and/or vinyl polymers or copolymers, acrylic-silicone copolymers, polyacrylamides, silicone polymers, fluorinated polymers, and mixtures thereof.

7. The composition of claim 2, wherein the polymer is selected from the group consisting of polyurethanes, acrylic polyurethanes, polyureas, polyurea-polyurethanes, polyester-polyurethanes, polyether-polyurethanes, polyesters, polyester amides, fatty chain polyesters, alkyds, acrylic and/or vinyl polymers or copolymers, acrylic-silicone copolymers, polyacrylamides, silicone polymers, fluorinated polymers, and mixtures thereof.

8. The composition of claim 3, wherein the polymer is selected from the group consisting of polyurethanes, acrylic polyurethanes, polyureas, polyurea-polyurethanes, polyester-polyurethanes, polyether-polyurethanes, polyesters, polyester amides, fatty chain polyesters, alkyds, acrylic and/or vinyl polymers or copolymers, acrylic-silicone copolymers, polyacrylamides, silicone polymers, fluorinated polymers, and mixtures thereof.

9. The composition of claim 1, wherein the liquid fatty phase comprises oils of inorganic, animal, plant or synthetic origin, carbonaceous oils, hydrocarbon oils, fluorinated oils and/or silicone oils, alone or in the form of a mixture.

10. The composition of claim 2, wherein the liquid fatty phase comprises oils of inorganic, animal, plant or synthetic origin, carbonaceous oils, hydrocarbon oils, fluorinated oils and/or silicone oils, alone or in the form of a mixture.

11. The composition of claim 3, wherein the liquid fatty phase comprises oils of inorganic, animal, plant or synthetic origin, carbonaceous oils, hydrocarbon oils, fluorinated oils and/or silicone oils, alone or in the form of a mixture.

12. The composition of claim 1, wherein the liquid fatty phase comprises paraffin oil or liquid petroleum jelly, vison oil, turtle oil, soya bean oil, perhydrosqualene, sweet almond oil, calophyllum oil, palm oil, parleam oil, grapeseed oil, sesame oil, maize oil, rapeseed oil, sunflower oil, cottonseed oil, apricot oil, castor oil, avocado oil, jojoba oil, olive oil or cereal germ oil, esters of lanolic acid, oleic acid, lauric acid or stearic acid; fatty esters, higher fatty acids or fatty alcohols, silicone oils, polysiloxanes modified with fatty acids, fatty alcohols or polyoxy alkylenes, fluorinated silicones and perfluorinated oils, or volatile oils.

13. The composition of claim 2, wherein the liquid fatty phase comprises paraffin oil or liquid petroleum jelly, vison oil, turtle oil, soya bean oil, perhydrosqualene, sweet almond oil, calophyllum oil, palm oil, parleam oil, grapeseed oil, sesame oil, maize oil, rapeseed oil, sunflower oil, cottonseed oil, apricot oil, castor oil, avocado oil, jojoba oil, olive oil or cereal germ oil, esters of lanolic acid, oleic acid, lauric acid or stearic acid; fatty esters, higher fatty acids or fatty alcohols, silicone oils, polysiloxanes modified with fatty acids, fatty alcohols or polyoxy alkylenes, fluorinated silicones and perfluorinated oils, or volatile oils.

14. The composition of claim 3, wherein the liquid fatty phase comprises paraffin oil or liquid petroleum jelly, vison oil, turtle oil, soya bean oil, perhydrosqualene, sweet almond oil, calophyllum oil, palm oil, parleam oil, grapeseed oil, sesame oil, maize oil, rapeseed oil, sunflower oil, cottonseed oil, apricot oil, castor oil, avocado oil, jojoba oil, olive oil or cereal germ oil, esters of lanolic acid, oleic acid, lauric acid or stearic acid; fatty esters, higher fatty acids or fatty alcohols, silicone oils, polysiloxanes modified with fatty acids, fatty alcohols or polyoxy alkylenes, fluorinated silicones and perfluorinated oils, or volatile oils.

15. The composition of claim 1, wherein the liquid fatty phase comprises:
  (a) nonaqueous liquid compounds having an overall solubility parameter according to the HANSEN solubility space of less than 17 $(Mpa)^{1/2}$,
  (b) monoalcohols having an overall solubility parameter according to the HANSEN solubility space of less than or equal to 20 $(MPa)^{1/2}$, or
  (c) mixtures thereof.

16. The composition of claim 2, wherein the liquid fatty phase comprises:
  (a) nonaqueous liquid compounds having an overall solubility parameter according to the HANSEN solubility space of less than 17 $(MPa)^{1/2}$,
  (b) monoalcohols having an overall solubility parameter according to the HANSEN solubility space of less than or equal to 20 $(MPa)^{1/2}$, or
  (c) mixtures thereof.

17. The composition of claim 3, wherein the liquid fatty phase comprises:
  (a) nonaqueous liquid compounds having an overall solubility parameter according to the HANSEN solubility space of less than 17 $(MPa)^{1/2}$,
  (b) monoalcohols having an overall solubility parameter according to the HANSEN solubility space of less than or equal to 20 $(MPa)^{1/2}$, or
  (c) mixtures thereof.

18. The composition of claim 1, wherein the nonvolatile liquid fatty phase contains at least one apolar or weakly polar oil.

19. The composition of claim 2, wherein the nonvolatile liquid fatty phase contains at least one apolar or weakly polar oil.

20. The composition of claim 3, wherein the nonvolatile liquid fatty phase contains at least one apolar or weakly polar oil.

21. The composition of claim 1, wherein the nonvolatile liquid fatty phase comprises at most 30% of the total weight of the composition.

22. The composition of claim 2, wherein the nonvolatile liquid fatty phase comprises at most 30% of the total weight of the composition.

23. The composition of claim 3, wherein the nonvolatile liquid fatty phase comprises at most 30% of the total weight of the composition.

24. The composition of claim 1, wherein the stabilizer is selected from the group consisting of block polymers, graft polymers, random polymers and mixtures thereof.

25. The composition of claim 2, wherein the stabilizer is selected from the group consisting of block polymers, graft polymers, random polymers and mixtures thereof.

26. The composition of claim 3, wherein the stabilizer is selected from the group consisting of block polymers, graft polymers, random polymers and mixtures thereof.

27. The composition of claim 1, wherein the stabilizer is selected from the group consisting of silicone polymers grafted with a hydrocarbon chain; hydrocarbon polymers grafted with a silicone chain; graft copolymers having a polyacrylic insoluble skeleton with soluble graft units of polyhydroxystearic acid; block or graft block copolymers comprising at least one block of polyorganosiloxane and at least one block of a free-radical polymer; block or graft block copolymers comprising at least one block of polyorganosiloxane and at least one polyether; copolymers of acrylates or methacrylates of $C_1$–$C_4$ alcohols, or of acrylates or methacrylates of $C_8$–$C_{30}$ alcohols; block or graft block copolymers comprising at least one block resulting from the polymerization of diene and at least one block of a vinyl polymer; block or graft block copolymers comprising at least one block resulting from the polymerization of diene and at least one block of an acrylic polymer; block or graft block copolymers comprising at least one block resulting from the polymerization of diene and at least one block of a polyether.

28. The composition of claim 2, wherein the stabilizer is selected from the group consisting of silicone polymers grafted with a hydrocarbon chain; hydrocarbon polymers grafted with a silicone chain; graft copolymers having a polyacrylic insoluble skeleton with soluble graft units of polyhydroxystearic acid type; block or graft block copolymers comprising at least one block of polyorganosiloxane and at least one block of a free-radical polymer; block or graft block copolymers comprising at least one block of polyorganosiloxane and at least one polyether; copolymers of acrylates or methacrylates of $C_1$–$C_4$ alcohols, or of acrylates or methacrylates of $C_8$–$C_{30}$ alcohols; block or graft block copolymers comprising at least one block resulting from the polymerization of diene and at least one block of a vinyl polymer; block or graft block copolymers comprising at least one block resulting from the polymerization of diene and at least one block of an acrylic polymer; block or graft block copolymers comprising at least one block resulting from the polymerization of diene and at least one block of a polyether.

29. The composition of claim 3, wherein the stabilizer is selected from the group consisting of silicone polymers grafted with a hydrocarbon chain; hydrocarbon polymers grafted with a silicone chain; graft copolymers having a polyacrylic insoluble skeleton with soluble graft units of polyhydroxystearic acid; block or graft block copolymers comprising at least one block of polyorganosiloxane and at least one block of a free-radical polymer; block or graft block copolymers comprising at least one block of polyorganosiloxane and at least one polyether; copolymers of acrylates or methacrylates of $C_1$–$C_4$ alcohols, or of acrylates or methacrylates of $C_8$–$C_{30}$ alcohols; block or graft block copolymers comprising at least one block resulting from the polymerization of diene and at least one block of a vinyl polymer; block or graft block copolymers comprising at least one block resulting from the polymerization of diene and at least one block of an acrylic polymer; block or graft block copolymers comprising at least one block resulting from the polymerization of diene and at least one block of a polyether.

30. The composition of claim 1, wherein the stabilizer is a block or graft block polymer comprising at least one block resulting from the polymerization of diene and at least one block of a vinyl polymer.

31. The composition of claim 2, wherein the stabilizer is a block or graft block polymer comprising at least one block resulting from the polymerization of diene and at least one block of a vinyl polymer.

32. The composition of claim 3, wherein the stabilizer is a block or graft block polymer comprising at least one block resulting from the polymerization of diene and at least one block of a vinyl polymer.

33. The composition of claim 1, further comprising at least one additional fatty phase selected from the group consisting of waxes, gums and/or pasty fatty substances of plant, animal, inorganic or synthetic origin, or containing silicone, and mixtures thereof.

34. The composition of claim 2, further comprising at least one additional fatty phase selected from the group consisting of waxes, gums and/or pasty fatty substances of plant, animal, inorganic or synthetic origin, or containing silicone, and mixtures thereof.

35. The composition of claim 3, further comprising at least one additional fatty phase selected from the group consisting of waxes, gums and/or pasty fatty substances of plant, animal, inorganic or synthetic origin, or containing silicone, and mixtures thereof.

36. The composition of claim 1, wherein the coloring agent comprises pulverulent compounds selected from the group consisting of fillers and/or pigments and/or pearlescent agents.

37. The composition of claim 36, wherein the pulverulent compounds represent up to 20 40% of the total weight of the composition.

38. The composition of claim 37, wherein the pulverulent compounds represent from 1 to 30% of the total weight of the composition.

39. The composition of claim 1, wherein the nonvolatile liquid fatty components, as dry matter, weight ratio ranges from 0.30 to 60.

40. The composition of claim 1, wherein the liquid fatty phase contains at least one volatile oil chosen from $C_8$–$C_6$ isoparaffins and linear or cyclic silicones having from 2 to 7 silicon atoms, these silicones optionally comprising alkyl groups having from 1 to 10 carbon atoms, and mixtures thereof.

41. The composition of claim 1, provided in the form of a stick or rod; in the form of a soft paste, with a dynamic viscosity at 25° C. of the order of 1 to 40 Pa.s; in the form of a dish; of an oily gel; of an oily liquid, of a vesicular dispersion containing ionic and/or nonionic lipids.

42. The composition of claim 1, provided in anhydrous form.

43. The composition of claim 1, provided in the form of a care and/or make-up product for the skin and/or the lips.

44. The composition of claim 1, provided in the form of a cast foundation, a cast blusher or eyeshadow, a lipstick, a care base or balm for the lips, or a concealer.

45. A method of producing the composition of claim 1, comprising combining the liquid fatty phase, the non-film forming-polymer and the coloring agent.

46. A method of producing the composition of claim 2, comprising combining the liquid fatty phase, the solid wax, and the non-film forming-polymer.

47. A method of producing the composition of claim 3, comprising combining the liquid fatty phase, the non-film forming-polymer and the active agent.

48. A method of forming a film on skin or lips, comprising applying a film-forming effective amount of the composition of claim 1 to the skin or lips.

49. A method of forming a film on skin or lips, comprising applying a film-forming effective amount of the composition of claim 2 to the skin or lips.

50. A method of forming a film on skin or lips, comprising applying a film-forming effective amount of the composition of claim 3 to the skin or lips.

51. A method of limiting, or suppressing, the transfer of a make-up or care composition for the skin or the lips onto a support different from the skin or lips, wherein the make-up or care composition contains a liquid fatty phase and at least one ingredient selected from the group consisting of coloring agents, cosmetic active agents, dermatological active agents, hygienic active agents, pharmaceutical active agents, and mixtures thereof, comprising introducing into the liquid fatty phase 2 to 60% by weight, relative to the total weight of the make-up or care composition, of surface-stabilized non-film-forming polymer particles, which polymer particles are dispersed in said fatty phase and stabilized at their surface, wherein the polymer is selected from the group consisting of radical polymers. polycondensates and polymers of natural origin, and mixtures thereof; wherein at most 40% by weight, relative to the total weight of the composition, is nonvolatile.

52. The composition of claim 39, Wherein the nonvolatile liquid fatty components, as dry matter, weight ratio ranges from 0.40 to 0.45.

53. The composition of claim 4, wherein the coloring agent comprises pulverulent compounds selected from the group consisting of fillers, pigments, pearlescent agents and combinations thereof.

54. The composition of claim 5, wherein the coloring agent comprises pulverulent compounds selected from the group consisting of fillers, pigments, pearlescent agents and combinations thereof.

55. The composition of claim 2, wherein the coloring agent comprises pulverulent compounds selected from the group consisting of fillers, pigments, pearlescent agents and combinations thereof.

56. The composition of claim 55, wherein the pulverulent compounds represent up to 40% of the total weight of the composition.

57. The composition of claim 56, wherein the pulverulent compounds represent from 1 to 30% of the total weight of the composition.

58. The composition of claim 2, wherein the nonvolatile liquid fatty components, as dry matter, weight ratio ranges from 0.30 to 0.60.

59. The composition of claim 58, wherein the nonvolatile liquid fatty components, as dry matter, weight ratio ranges from 0.40 to 0.45.

60. The composition of claim 2, wherein the liquid fatty phase contains at least one volatile oil selected from the group consisting of from $C_8$–$C_{16}$ isoparaffins and linear or cyclic silicones having from 2 to 7 silicon atoms, these silicones optionally comprising alkyl groups having from 1 to 10 carbon atoms, and mixtures thereof.

61. The composition of claim 2, provided in the form of a stick or rod; in the form of a soft paste, with a dynamic viscosity at 25° C. of the order of 1 to 40 Pa.s; in the form of a dish; of an oily gel; of an oily liquid, of a vesicular dispersion containing ionic and/or nonionic lipids.

62. The composition of claim 2, provided in anhydrous form.

63. The composition of claim 2, provided in the form of a care and/or make-up product for the skin and/or the lips.

64. The composition of claim 2, provided in the form of a cast foundation, a cast blusher or eyeshadow, a lipstick, a care base or balm for the lips, or a concealer.

65. The composition of claim 3, wherein the nonvolatile liquid fatty components, as dry matter, weight ratio ranges from 0.30 to 0.60.

66. The composition of claim 3, wherein the nonvolatile liquid fatty components, as dry matter, weight ratio ranges from 0.40 to 0.45.

67. The composition of claim 3, wherein the liquid fatty phase contains at least one volatile oil selected from the group consisting of from $C_8$–$C_{16}$ isoparaffins and linear or cyclic silicones having from 2 to 7 silicon atoms, these silicones optionally comprising alkyl groups having from 1 to 10 carbon atoms, and mixtures thereof.

68. The composition of claim 3, provided in the form of a stick or rod; in the form of a soft paste, with a dynamic viscosity at 25° C. of the order of 1 to 40 Pa.s; in the form of a dish; of an oily gel; of an oily liquid, of a vesicular dispersion containing ionic and/or nonionic lipids.

69. The composition of claim 3, provided in anhydrous form.

70. The composition of claim 3, provided in the form of a care and/or make-up product for the skin and/or the lips.

71. The composition of claim 3, provided in the form of a cast foundation, a cast blusher or eyeshadow, a lipstick, a care base or balm for the lips, or a concealer.

72. The composition of claim 1, wherein the pigment/polymer weight ratio is <1.

73. The composition of claim 1, wherein the pigment/polymer weight ratio is $\leq 0.9$.

* * * * *